United States Patent
Jank et al.

(10) Patent No.: US 11,906,462 B2
(45) Date of Patent: Feb. 20, 2024

(54) SYSTEM FOR DETERMINING AND/OR MONITORING A STATE VARIABLE OF A MEASUREMENT OBJECT AND RESPECTIVE METHOD

(71) Applicant: Fraunhofer-Gesellschaft zur Foerderung der angewandten Forschung e.V., Munich (DE)

(72) Inventors: Michael Jank, Erlangen (DE); Susanne Oertel, Pettstadt (DE); Alicia Marion Zoerner, Erlangen (DE); Wolfgang Thieme, Schwaig (DE); Thomas Heckel, Erlangen (DE); Christopher Joffe, Erlangen (DE); Esther Ann Renner, Erlangen (DE); Christian Hofmann, Nuremberg (DE); Nadine Ramona Lang, Erlangen (DE); Matthias Struck, Nuremberg (DE); Achim Endruschat, Pilsach (DE); Holger Gerstner, Erlangen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1194 days.

(21) Appl. No.: 16/514,869

(22) Filed: Jul. 17, 2019

(65) Prior Publication Data
US 2019/0339225 A1    Nov. 7, 2019

Related U.S. Application Data

(63) Continuation of application No. PCT/EP2018/051191, filed on Jan. 17, 2018.

(30) Foreign Application Priority Data

Jan. 19, 2017    (DE) .......................... 102017200884.9
Jul. 3, 2017    (DE) .......................... 102017211282.4

(51) Int. Cl.
*G01N 27/333*    (2006.01)
*G01N 33/18*    (2006.01)
*G01N 33/24*    (2006.01)

(52) U.S. Cl.
CPC .......... *G01N 27/333* (2013.01); *G01N 33/18* (2013.01); *G01N 33/24* (2013.01); *G01N 2033/245* (2013.01)

(58) Field of Classification Search
CPC ...... G01N 27/333; G01N 33/18; G01N 33/24; G01N 2033/245
See application file for complete search history.

(56) References Cited

U.S. PATENT DOCUMENTS 5,993,742 A    11/1999    Binz et al.
9,046,461 B1    6/2015    Sohrabi et al.
(Continued)

FOREIGN PATENT DOCUMENTS

DE    102010015551 A1    10/2011
EP    0821231 B1    12/2003
(Continued)

OTHER PUBLICATIONS

Nguyen, Cuong M., et al. "Wireless sensor nodes for environmental monitoring in Internet of Things." 2015 IEEE MTT-S International Microwave Symposium. IEEE, 2015. (Year: 2015).*
(Continued)

*Primary Examiner* — Robert J Eom
(74) *Attorney, Agent, or Firm* — Perkins Cole LLP; Michael A. Glenn

(57) ABSTRACT

The invention relates to a system for determining and/or monitoring a state variable of a measurement object comprising an analysis sensor, a control apparatus and a read-out apparatus. The analysis sensor is configured to be introducible into the measurement object for remaining within the (Continued)

same, to be sensitive to an ion type and to generate measurement data based on a concentration of the ion type in the measurement object. The control apparatus controls the analysis sensor with respect to the generation of the measurement data. The read-out apparatus reads the measurement data out of the analysis sensor. Further, the invention relates to a respective method.

15 Claims, 3 Drawing Sheets

(56) References Cited

U.S. PATENT DOCUMENTS

| | | |
|---|---|---|
| 2012/0063334 A1 | 3/2012 | Drake |
| 2012/0319866 A1 | 12/2012 | Svoen et al. |
| 2015/0087072 A1 | 3/2015 | Adamchuk et al. |
| 2015/0150505 A1 | 6/2015 | Kaskoun et al. |
| 2016/0169855 A1 | 6/2016 | Baity |
| 2016/0327511 A1 | 11/2016 | Wenzel et al. |

FOREIGN PATENT DOCUMENTS

| | | |
|---|---|---|
| EP | 2450703 A1 | 5/2012 |
| EP | 1840566 B1 | 12/2012 |
| EP | 2980576 A1 | 2/2016 |
| EP | 3225978 A1 | 10/2017 |
| WO | 2011127905 A1 | 10/2011 |
| WO | 2014096844 A1 | 6/2014 |
| WO | 2014113460 A1 | 7/2014 |
| WO | 2014176179 A2 | 10/2014 |
| WO | 2016083649 A1 | 6/2016 |
| WO | 2016090176 A1 | 6/2016 |

OTHER PUBLICATIONS

Nrf51822 Product Brief, Nordic Semiconductor, https://nsscprodmedia.blob.core.windows.net/prod/software-and-other-downloads/product-briefs/nrf51822-product-brief.pdf , p. 1-2. (Year: NA).*

Atkinson, John K., and Marios Sophocleous. "A novel thick-film screen printed electrical conductivity sensor for measurement of liquid and soil conductivity." Sensors, 2014 IEEE. IEEE, 2014. (Year: 2014).*

Long, Robert, and Eric Bakker. "Spectral Imaging and Electrochemical Study on the Response Mechanism of Ionophore-Based Polymeric Membrane Amperometric pH Sensors." Electroanalysis: An International Journal Devoted to Fundamental and Practical Aspects of Electroanalysis 15.15-16 (2003): 1261-1269. (Year: 2003).*

Guinovart, Tomas et al., "A potentiometric tattoo sensor for monitoring ammonium in sweat", The Royal Society of Chemistry 2013, Analyst, 2013, 138, 2013, 7031-7038.

Guinovart, Tomas et al., "Potentiometric sensors using cotton yarns, carbon nanotubes and polymeric membranes", The Royal Society of Chemistry 2013, Analyst, 2013, 138, 2013, 5208-5215.

* cited by examiner

SYSTEM FOR DETERMINING AND/OR MONITORING A STATE VARIABLE OF A MEASUREMENT OBJECT AND RESPECTIVE METHOD

CROSS-REFERENCE TO RELATED APPLICATIONS

This application is a continuation of copending International Application No. PCT/EP2018/051191, filed Jan. 17, 2018, which is incorporated herein by reference in its entirety, and additionally claims priority from German Applications No. 102017200884.9, filed Jan. 19, 2017, and 102017211282.4, filed Jul. 3, 2017, which are all incorporated herein by reference in their entirety.

The invention relates to a system for determining and/or monitoring at least one state variable of a measurement object. Further, the invention relates to a method for determining and/or monitoring at least one state variable of a measurement object.

BACKGROUND OF THE INVENTION

Due to legal requirements it is obligatory, for example in agriculture, to monitor or control the state of soils or bodies of water. This serves to maintain water quality or to prevent overfertilization.

Two methods are known for analyzing soils and bodies of water: In one variation, a sample of the soil or the water is taken and sent to a laboratory. This is exact but also expensive. Additionally, it takes a certain time until the results are available. Above that, there is the possibility that the samples are made unusable due to shipment, are contaminated or are swapped in the laboratory. Alternatively, a swab can be taken directly at the measurement object with a test stick. This yields only a very coarse evaluation.

SUMMARY

According to one embodiment, a system for determining and/or monitoring at least one state variable of a measurement object may have: at least one analysis sensor, a control apparatus and a read-out apparatus, wherein the analysis sensor is configured to be introducible into the measurement object for remaining within the same and to be sensitive to at least one ion type and to generate measurement data in the measurement object based on a concentration of the ion type, wherein the control apparatus is configured to control the analysis sensor with respect to the generation of the measurement data, wherein the read-out apparatus is configured to read out the measurement data from the analysis sensor, and including a permanent individual network with a common central network node, wherein several analysis sensors that are sensitive to the same ion type or to different ion types exist, wherein the several analysis sensors are configured to be read-out via the common central network node, wherein the read-out apparatus includes a first read-out unit and a second read-out unit, wherein the first read-out unit is configured as the common central network node, and wherein the second read-out unit is a mobile read-out unit disposed outside the measurement object that is configured to communicate wirelessly with the first read-out unit introduced into the measurement object, wherein the analysis sensors and the first read-out unit are configured to be permanently buried within the measurement object, wherein the system further includes at least one energy source that is configured to supply at least one analysis sensor with energy, wherein the energy source includes at least one accumulator and wherein the energy source is configured such that the accumulator can be charged inductively.

The system comprises at least one analysis sensor, a control apparatus and a read-out apparatus. The analysis sensor is configured to be introduced into the measurement object for remaining within the same. The analysis sensor is configured to be sensitive to at least one ion type and to generate measurement data in the measurement object based on a concentration of the ion type. The control apparatus is configured to control the analysis sensor with regard to the generation of measurement data. The read-out apparatus is configured to read out the measurement data from the analysis sensor.

Thus, the analysis sensor in particular allows the measurement of ions, wherein the analysis sensor reacts specifically to at least one—alternatively only one—ion type. Here, the ion type is in indirect or direct connection with the state variable of the measurement object to be determined and/or to be monitored, such that also the measurement data of the analysis sensor are in indirect or in direct connection with the state variable.

The analysis sensor is configured such that the same is introduced into the measurement object in order to remain within the same. Thus, not only a single measurement is preformed but a permanent measurement system is provided.

Depending on the configuration, the system provides a possibility of a continuous, fast, real-time able measurement of ions in a measurement substance of the measurement object. This serves, for example, to control soils or water quality. Depending on the configuration, in particular by using an evaluation apparatus, direct fast evaluation or even feedback in real-time results. Above that, there are the advantages of direct sample collection and direct evaluation. If several analysis sensors are used, for example, large agricultural areas can be monitored without continuous personnel support.

Three variations for the measurement object will be described whose state variables are to be determined or to be monitored.

In one configuration, the measurement object is a soil. The soil is, for example, farmland, a meadow or a field.

In a further configuration, the measurement object is a body of water. The water is, for example, a river, a pond, a lake or a clarifying tank, etc. The analysis sensor or possibly the analysis sensors are within water pipes, taps, domestic water works, water works, wells, deep wells, pumps, heating systems, water conditioners, water filters, water meters, swimming pools, reservoirs, lakes and bodies of water, rivers, streams, etc. However, applications also relate to private usage, e.g. swimming pools. In a different configuration, the measurement object is an agricultural product. The agricultural product is, for example, fruit or vegetable or it is biomass for energy generation. Further, it can be feedstuff in the form of silage.

One state variable is, for example, the nitrate content for which legal requirements exist in agriculture. For example, the nitrate concentration in wells or drinking water plants has to be controlled regularly, wherein allowed limits may not be exceeded. In the context of nitrogen balance, fields may only be fertilized up to an allowed maximum limit per area and per year.

Further state parameters are, for example ammonium concentration or ammonia concentration: These parameters are very well suited as indicators for contaminations of bodies of water by domestic waste water and agricultural production. Ammonium is a non-toxic plant nutrient. Ammonia, on the other hand, is a colorless pungently smelling poisonous gas. Both forms coexist in water. Here, the relation to the pH value is of importance. The pH value is determined, for example, by an additional sensor presented below. A balanced ratio between ammonium and ammonia exists around the neutral point 7.0. If the pH value moves to the alkaline (basic milieu, ammonia is released from the ammonium ions. In strongly basic solutions, free ammonia exists, which is lethal for any life in the body of water at higher concentrations.

Further state variables are, for example the concentration and/or type of acids. Taking the example of silage, monitoring the pH value itself usually provides no sufficient statement on fermentation quality. Detecting several acid types (e.g. butyric, acetic and lactic acids) is needed.

Possible applications of the system in agriculture are, for example:
  Controlling the nitrogen content in the form of nitrate limits or determining the optimum time of sowing, wherein at least one analysis sensor is introduced into a humid soil.
  Monitoring water reservoirs that are used, for example, in agriculture.
  Monitoring ground water reserves influenced by agricultural areas.
  Monitoring slurry tanks as an example of carriers for agricultural products for evaluating the fertilization content prior to application onto the field.
  Controlling drinking and well water (legal requirement also for agricultural companies).
  Optimized fertilizer management.
  Monitoring silage containers.

In one configuration, several analysis sensors exist. Thus, the at least two analysis sensors are at the same or at different locations within the measurement object. In one configuration, the analysis sensors are read out individually. In a further configuration, the analysis sensors are read out via at least one common node. In one configuration, the read-out apparatus can be this common node or can comprise at least such a common node, for example in the form of a read-out unit as a part of the read-out apparatus. Here, the common node can be configured to be able to be introduced into the measurement object for remaining within the same. Thus, the analysis sensors and the common node for reading out the analysis sensors are introduced into the measurement object, wherein the analysis sensors, which can be distributed within the measurement object, can communicate within the measurement object with the common node arranged centrally in the measurement object.

In one configuration, it is intended that the analysis sensors are sensitive to the same ion type. Alternatively or additionally, in one configuration, it is intended that the analysis sensors are sensitive to different ion types. In one configuration, at least two analysis sensors are sensitive to the same ion type and at least one analysis sensor is sensitive to a different ion type.

In a further configuration, at least one analysis sensor is sensitive to at least two ion types. Such a multisensor provides measurement data on several ion types, for example in order to detect the interaction of different ions. Here, the measurement data can be interpreted via respective algorithms.

In one configuration, the system comprises at least one memory device.

In one configuration, the memory device serves to store evaluation data and/or reference data for evaluating the measurement data of the at least one analysis sensor. The memory device can be configured to be introduced into the measurement object for remaining within the same. The memory device can be connected to the read-out apparatus and can be introduced into the measurement object together with the same.

In an alternative or additional configuration, the memory device is configured to store the measurement data and/or data derived from the measurement data. In one configuration, the read-out apparatus is configured to read out measurement data from the at least one analysis sensor and to store the same in the memory device. The data derived from the measurement data are, for example, statements on the ions or the measurement medium in which the analysis sensor is located (e.g. the concentration of the ions) based on reference data are derived from the primary measurement data (e.g. a voltage value) based on reference data. Alternatively or additionally, the derived data are a measure for the changes of the measurement data of the at least one analysis sensor or a measure for the deviation between the measurement data of several analysis sensors.

According to one configuration, the system comprises at least one evaluation apparatus. In one configuration, the evaluation apparatus is configured to evaluate the measurement data of the at least one analysis sensor or alternatively the analysis sensors with respect to the state variable and/or to derive data from the measurement data. In one configuration, the evaluation apparatus is connected to the memory device and/or to the control apparatus and/or to the read-out apparatus. The evaluation apparatus can be configured to be introducible into the measurement object for remaining within the same. In one configuration, the evaluation apparatus can be introduced into the measurement object together with the memory device and/or the read-out apparatus. In one configuration, evaluation includes determining area-related concentration and/or change of concentration. In one configuration, if several analysis sensors are used, the evaluation includes determining a distribution of concentration.

One configuration intends that the system includes at least one additional sensor. In one configuration, the additional sensor is configured to generate measurement data at least in dependence on a temperature, fill level, flow rate (mass and/or volume flow rate), pH value, electric resistance, electric conductivity, proportion of a gas, proportion of oxygen (as selected gas) or flow velocity. Thus, the additional sensor differs from the analysis sensors and is not dependent on a specific ion type. In one configuration, the measurement data of the additional sensor relate to the measurement object (e.g. the temperature or the fill level in a container) itself, and in an alternative configuration to the environment of the measurement object (e.g. the amount of water flowing into the measurement object).

According to one configuration, the system includes at least one energy source. The energy source is configured to supply at least one analysis sensor with energy. Alternatively or additionally, the energy source serves to supply at least one of the read-out apparatus, the evaluation apparatus, the control apparatus or the memory device with energy.

The following configurations relate to the specific configuration of the energy source.

One configuration provides that the energy source comprises at least one battery.

Alternatively or additionally, one configuration is that the energy source comprises at least one accumulator. In an associated configuration, the energy source is configured such that the accumulation is rechargeable in a contactless manner. In one configuration, charging is performed by an inductive operating principle, wherein a respective electric circuit and/or the components for coupling in and converting the energy for charging the accumulator are attached to the accumulator.

According to an alternative or additional configuration, the energy source is configured to generate energy by means of energy harvesting. Wind energy or a temperature difference, for example, is used for this.

In one configuration, it is provided that at least one analysis sensor and the read-out apparatus are connected to one another in a wireless manner and/or by electromagnetic waves with respect to data transmission. Thus, in this configuration, there is no cable connection between at least one analysis sensor and the read-out apparatus. Alternatively or additionally, at least one analysis sensor and the control apparatus are in wireless contact to one another.

In one configuration, data are transmitted by means of Bluetooth Low Energy, in particular across short distances. In a further configuration, the communicating components have antennas also allowing data transmission across longer distances.

In one configuration, the read-out apparatus is configured as mobile unit. In this configuration, for example, the read-out apparatus is brought close to the analysis sensors located within the measurement object, and possibly the at least one additional sensor, and the measurement data are read out. Advantageously, the mobile unit comprises at least one antenna for receiving the data.

In a further configuration, the read-out apparatus can comprise a first, possibly central, read-out unit that is configured to be introduced into the measurement object for remaining within the same. In such a configuration, the central first read-out unit introduced into the measurement object can centrally read out the analysis sensors also located within the measurement object. In this configuration, the read-out apparatus can further comprise a second, possibly mobile, read-out unit. The mobile second read-out unit can be located outside the measurement object and can communicate with the central first read-out unit located within the measurement object.

The following configurations relate to the specific configuration of the at least one analysis sensor.

According to one configuration, at least one analysis sensor comprises at least one ion-sensitive electrode printed on a flexible foil, e.g. by screen-printing pastes, an ion-selective membrane comprising at least one ionophore, a reference electrode and a counter electrode. Here, the ionophore serves to transport the allocated ion type through the membrane, which is therefore ion-selective. Here, the analysis sensor is inexpensive.

An ion-selective electrode (other designations are: ion-specific or ion-sensitive electrode) allows the measurement of the concentration or activity of a specific dissolved ion. Here, an electric voltage between the ion-selective electrode and a second electrode (the reference electrode) is measured. In one configuration, the foil is at least partly made of polyester (PET or PEN) or of polyimides (PI) or other synthetic materials, such as polyurethane (PU) or of synthetic textiles. If different ion types pass a membrane, respective calibration data allow a compensation of the measurement values.

Advantageously, this is a printed analysis sensor comprising printed working and reference electrodes as well as at least one passivation layer. The production is performed with commercially available screen-printing pastes, wherein in one configuration the printed electrodes are optimized by means of annealing at paste-specific temperatures. In one configuration, finishing the reference electrode includes depositing a mixture of polyvinyl butyral, methanol and sodium chloride (cf. T. Guinovart et al., "Potentiometric sensors using cotton yarns, carbon nanotubes and polymeric membranes", Analyst, 2013, 5208-5215). In one configuration, producing the first sensor includes applying the ion-selective material in the form of an ionophore (for example nonactin, valinomycin, sodium ionophore) on a working electrode. Here, in one configuration, a mixture with a matrix (network-forming materials, in particular polymers and advantageously polyvinyl butyral, PVB and polyvinyl chloride, PVC) is provided. In one configuration, the amount of ionophore is minimized for enabling inexpensive realization of the analysis sensor.

According to one configuration, at least one analysis sensor is configured to be sensitive to at least one ion type in a humid or wet environment. Therefore, the analysis sensor is configured, for example, to be able to measure the respectively relevant ions or substances in liquids or humid soils.

In one configuration, at least one analysis sensor allows a measurement of at least one of the following substances and/or their degradation products: nitrate, nitrite, chloride, fluoride, sulfate, ammonium, oxygen, phosphates, potassium, sodium or calcium.

Alternatively or additionally, the analysis sensor allows a measurement of at least one acid and/or of at least one degradation product in a fermentation process.

In one configuration, at least one analysis sensor is configured to allow a measurement of at least one of a biocide, a plasticizer, algae, fungi, spores, bacteria, a toxic agent, a toxin or a metallic substance. Thus, the measurement relates to one of the above-stated state variables.

Here, at least one analysis sensor is configured to continuously generate measurement data or to generate measurement data only at predeterminable measurement times.

In one configuration, at least one analysis sensor is configured such that the analysis sensor is biodegradable. Thus, the analysis sensor can completely remain within the measurement object until the same dissolves.

In one configuration, at least one analysis sensor comprises an identification unit. In one configuration, the identification unit is an RFID tag and in an alternative configuration, the same is a sign or a label with a serial number.

Further, the invention relates to a method for determining and/or monitoring at least one state variable of a measurement object.

The method includes at least the following steps:
introducing at least one analysis sensor into the measurement object for remaining within the same,
generating measurement data by the analysis sensor based on a concentration of an ion type in the measurement object,
controlling the analysis sensor with respect to the generation of the measurement data, and
reading out the measurement data from the analysis sensor.

Here, the measurement data are in particular in the context of the state variable and allow evaluation with respect to the state variable.

The above-described configurations of the apparatus can also be realized by the method, such that the configurations and statements apply accordingly to the method. Thus, repetitions are omitted.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
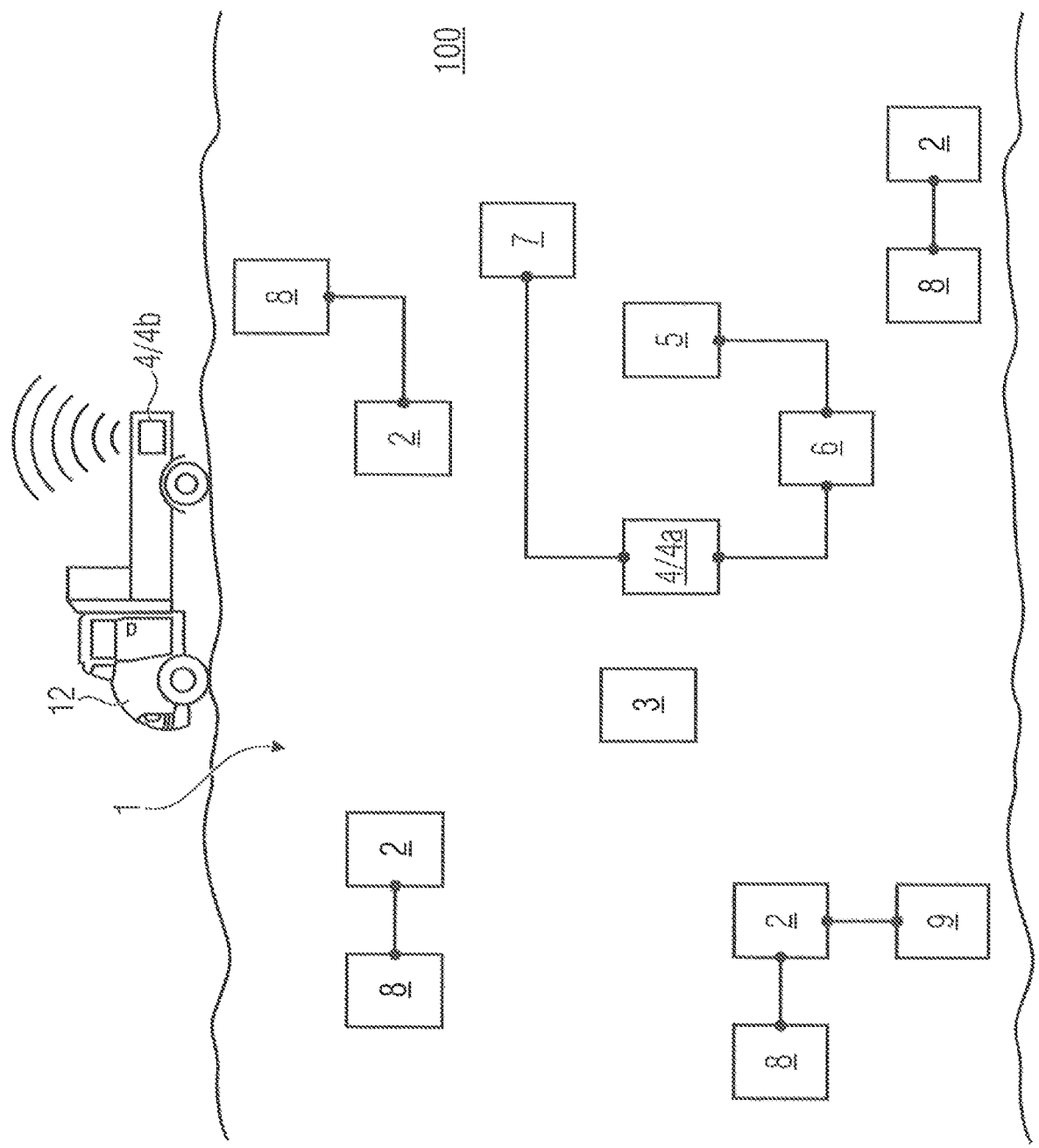
FIG. 1 is a schematic illustration of an example of the application of the system as a block diagram.

FIG. 1 schematically illustrates an application example of system 1. Here, a state variable of a soil as measurement object 100 is monitored or determined. As an example, the state variable is the exposure of the soil to fertilizer.

In this example, the system 1 comprises four analysis sensors 2 that are introduced into the soil 100 in order to remain there permanently and to generate measurement data.

Here, the analysis sensors 2 react to ions that are located in particular within a wet or at least humid environment.

In the shown configuration, each analysis sensor 2 has an energy source 8 for measurements and for the communication of the measurement data. The energy sources 8 are accumulators that can be charged in a contactless manner by means of the inductive operating principle and the allocated electric circuit and components. Further, an analysis sensor 2 has an identification unit 9 via which, for example, the position of the analysis sensor 2 can be identified additionally by means of GPS technology. The other analysis sensors 2 can be identified, for example, via their serial numbers.

The measurements of the analysis sensors 2 are controlled by a control apparatus 3, in particular communicating via radio with the analysis sensors 2 and determining the measurement times and also monitoring the energy supply. The control apparatus 3 can also be introduced into the soil 100.

The control apparatus 3 is configured to communicate with the analysis sensors 2 and to initiate and/or to coordinate a measurement to be performed by means of the analysis sensors 2.

In an alternative configuration, the control apparatus 3 can be omitted. In such a case, the analysis sensors 2 can have an integrated control. Here, the integrated control could be configured to initiate a measurement in periodic time intervals. This could, for example, be a timer implemented in hardware or software.

In a further possible embodiment, the analysis sensors 2 could, for example, comprise an integrated intelligent control unit. Such a control unit could decide in an intelligent manner (for example based on feedback control circuits or a statistical evaluation of earlier measurement values) how often measurement values are to be collected. If, for example, in one section of the soil 100 hardly any changes occur, for example in the course of a year, less measurements can be performed/logged and less measurement points can be recorded in the following year. If, however, measurement values change more frequently and cover a large range of values, the measurements can be performed more frequently in future. The intelligent control can also be performed by incorporating further sensor data, such as sensors for precipitation, temperature and humidity that are also mounted in the soil portion 100 or on the soil or raised above the soil.

Further, a read-out apparatus 4, which in the example shown in FIG. 1 is firmly installed in the soil 100, is provided, which reads out the measurement data also in a contactless and here also in particular wireless manner and transmits the same to the evaluation apparatus 6. By using algorithms and/or reference data etc., the evaluation apparatus 6 evaluates the measurement data and derives data therefrom which are in connection with the state variable of the measurement object 100. That way, the generated data give information, for example on nitrate content in the soil 100. The generated (evaluation) data are stored in a memory device 5 by the evaluation apparatus 6.

The memory device 5 can be a central memory device where the data of one analysis sensor and advantageously all analysis sensors can be stored. Additionally or alternatively, each analysis sensor 2 can have its individual memory unit. When in that case the memory of one analysis sensor 2 fails, the individual analysis sensors 2 could communicate with one another and latch the data of the analysis sensor 2 having a defect memory.

Additionally, an additional sensor 7 is provided which provides further information on the measurement object 100. In the shown example, this is the pH value. The additional sensor 7 is also read out by the read-out apparatus 4 in order to transmit the measurement values with respect to the pH value to the evaluation apparatus 6. Thus, the measurement values of the additional sensor 7 are used together with the measurement data of the analysis sensor 2 for monitoring the state variable of the measurement object 1, here, for example, the contamination of the soil.

The read-out apparatus 4, the memory device 5, the evaluation apparatus 6 and the additional sensor 7 can all be introduced in the soil 100 and can remain therein.

In the embodiment shown in FIG. 1, at least two and advantageously all analysis sensors 2 communicate with the read-out apparatus 4. This means the read-out apparatus 4 can read out at least two and advantageously all analysis sensors 2. The read-out data can be stored in the memory device 5. Optionally, the read-out data can be evaluated by the evaluation apparatus 6 and the evaluated data can be stored in the memory device 5, alternatively or additionally to the read-out data.

Thus, a permanent independent network is provided within the measurement object 100, wherein the read-out apparatus 4 itself or at least a read-out unit 4a allocated to the read-out apparatus 4 forms a central network node for reading out the analysis sensors 2. In the embodiment shown in FIG. 1, the analysis sensors 2 and the read-out apparatus 4 can be permanently buried in the soil 100. In that way, an independent network is provided which is buried in the soil 100 and can permanently remain there.

As mentioned above, the read-out apparatus 4 can be arranged in the soil 100 in a stationary manner. In this case, for example, a cable could be routed to the surface above the soil in order to read out the data of the read-out apparatus 4 and/or the memory device 5 and/or the evaluation apparatus 6 in a stationary manner.

Alternatively or additionally, the read-out apparatus 4 can comprise at least two read-out units 4a, 4b that can communicate with one another in a wireless manner. Here, a first read-out unit 4a as illustrated in FIG. 1 would be introduced into the soil 100. A second read-out unit 4b could be arranged, for example, outside the measurement object 100 and could be configured as mobile read-out unit which can again be attached to a vehicle 12.

In this embodiment, the mobile second read-out unit 4b can communicate with the read-out unit 4a in the soil 100. As mentioned above, the first read-out unit 4a of the read-out apparatus 4 can form the central network node reading out at least two and advantageously all analysis sensors 2 in the soil. The central first read-out unit 4a can store all read-out data, also in a central manner, in the memory device 5 connected therewith. In that way, an independent network is provided within the measurement object 100.

As soon as the mobile second read-out unit 4b is close to the first read-out unit 4a buried in the soil 100, the two read-out units 4a, 4b can communicate with one another and the data read out before by means of the buried first read-out unit 4a (or stored in the memory device 5) can be transmitted to the mobile second read-out unit 4b outside or above the soil 100.

In an alternative embodiment, the read-out apparatus 4 comprises no separate read-out unit 4a to be introduced into the soil 100, but the same is attached directly as a mobile read-out apparatus outside the soil 100, for example to a vehicle. In that case, the analysis sensors 2 introduced into the soil 100 would all be read out individually by the read-out apparatus 4. Such an embodiment will be described in more detail below with reference to FIG. 2.

The embodiment shown in FIG. 1 has the advantage that at least 2 and advantageously all analysis sensors 2 buried in the soil can be read out by an individual central read-out unit 4a also buried in the soil, and the mobile second read-out unit 4b arranged outside the soil 100 then only has to read out the individual central read-out unit 4a buried in the soil. Thus, not each analysis sensor 2 has to be read out individually.

A further advantage is that the position of the central read-out unit 4a buried in the soil 100 could be marked at the surface of the soil 100, for example by a flag or the same. In a large field 100, the farmer could, for example, directly drive to this marked position and directly read out the central read-out unit 4a buried below the same. When the analysis sensors 2 all had to be read out individually, the farmer has to drive across the entire field 100 in order to ensure that he has read out all analysis sensors 2, since the analysis sensors 2 can be located anywhere across the field. Currently, this is rather the rule, since the analysis sensors 2 are designed as mobile units that can be distributed independently of one another at arbitrary locations in the field. When plowing the field, the analysis sensors 2 are even distributed further in an arbitrary manner. Even more, arbitrary distribution is desirable in order to obtain soil samples at very different locations of the soil 100.

Figure 2:
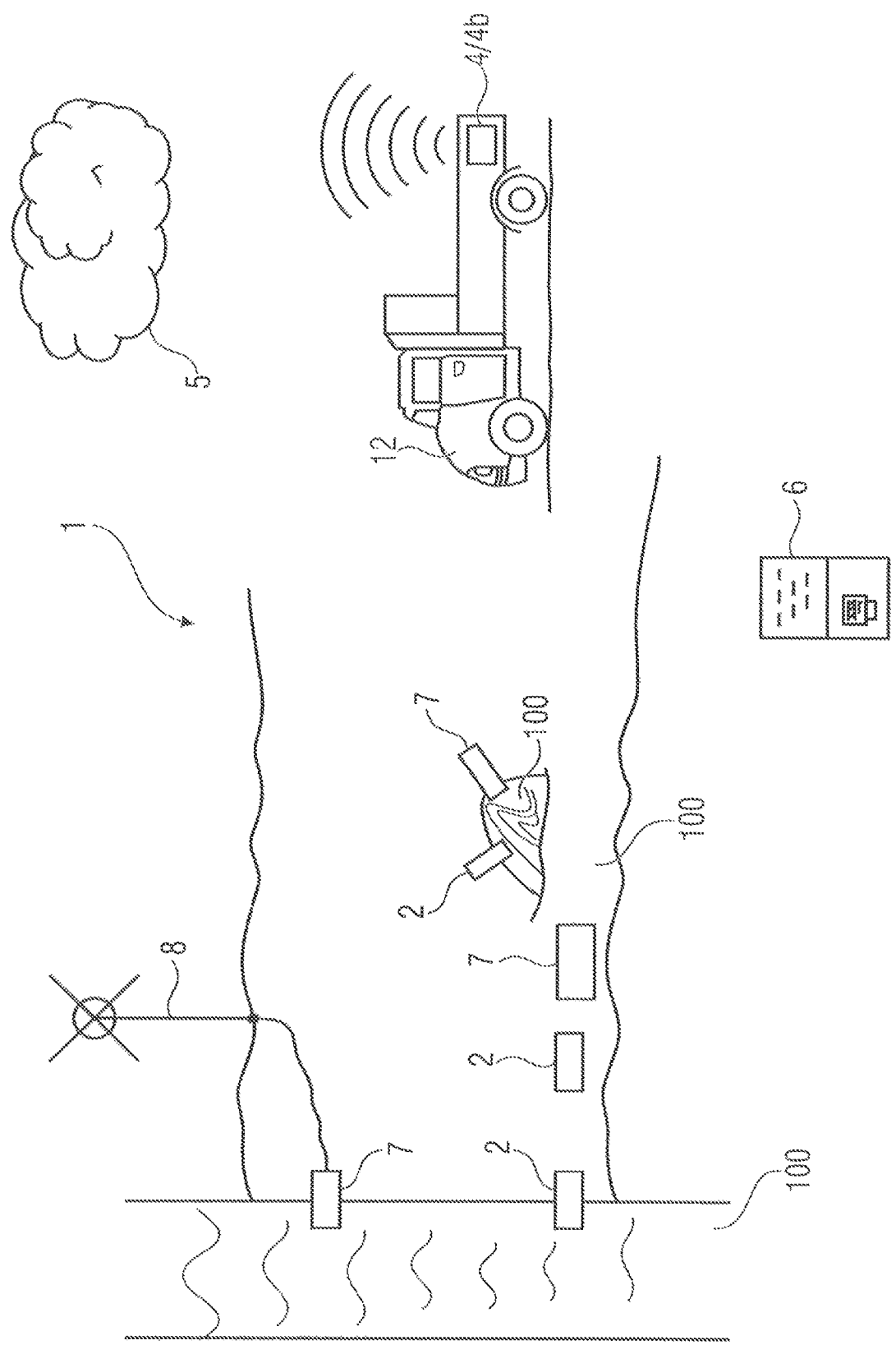
FIG. 2 is a schematic illustration of a further application example and FIG. 3 is a top view of an analysis sensor.

A further configuration of the system 1 is shown in FIG. 2. Here, three different measurement objections 100 are illustrated; a field as an example for soil, a river as an example for a body of water and a compost heap as an example for an agricultural product.

One analysis sensor 2 and one additional sensor 7 are each introduced into all three measurement objects 100. The additional sensor 7 of the river is, for example, a flow meter and the additional sensor 2 of the compost heap is a temperature measuring device. The additional sensor 7 of the soil 100 determines humidity.

Here, the flow meter 7 of the body of water 100 is connected to a wind wheel as an example for an energy source 8 performing energy harvesting.

Further, the read-out apparatus 4 is designed in a mobile manner and here, as one example, the same is moved by a tractor 12 through the area in which the measurement objects 100 reside. Here, in particular the read-out apparatus 4 is moved across the soil as measurement object 100. The read-out process is performed by applying RFID technology. The read-out apparatus 4 is connected to a memory device 5 via radio, here realized as cloud. As mentioned above, the read-out apparatus 4 can comprise a first read-out unit 4a firmly installed in the soil 100 as well as a mobile second read-out unit 4b. Accordingly, the example illustrated in FIG. 2 can also be a second read-out unit 4b attached to a tractor 12 as described above with reference to FIG. 1.

The further evaluation of the measurement data stored in the memory device 5 is performed by a computer as evaluation apparatus 6.

Figure 3:
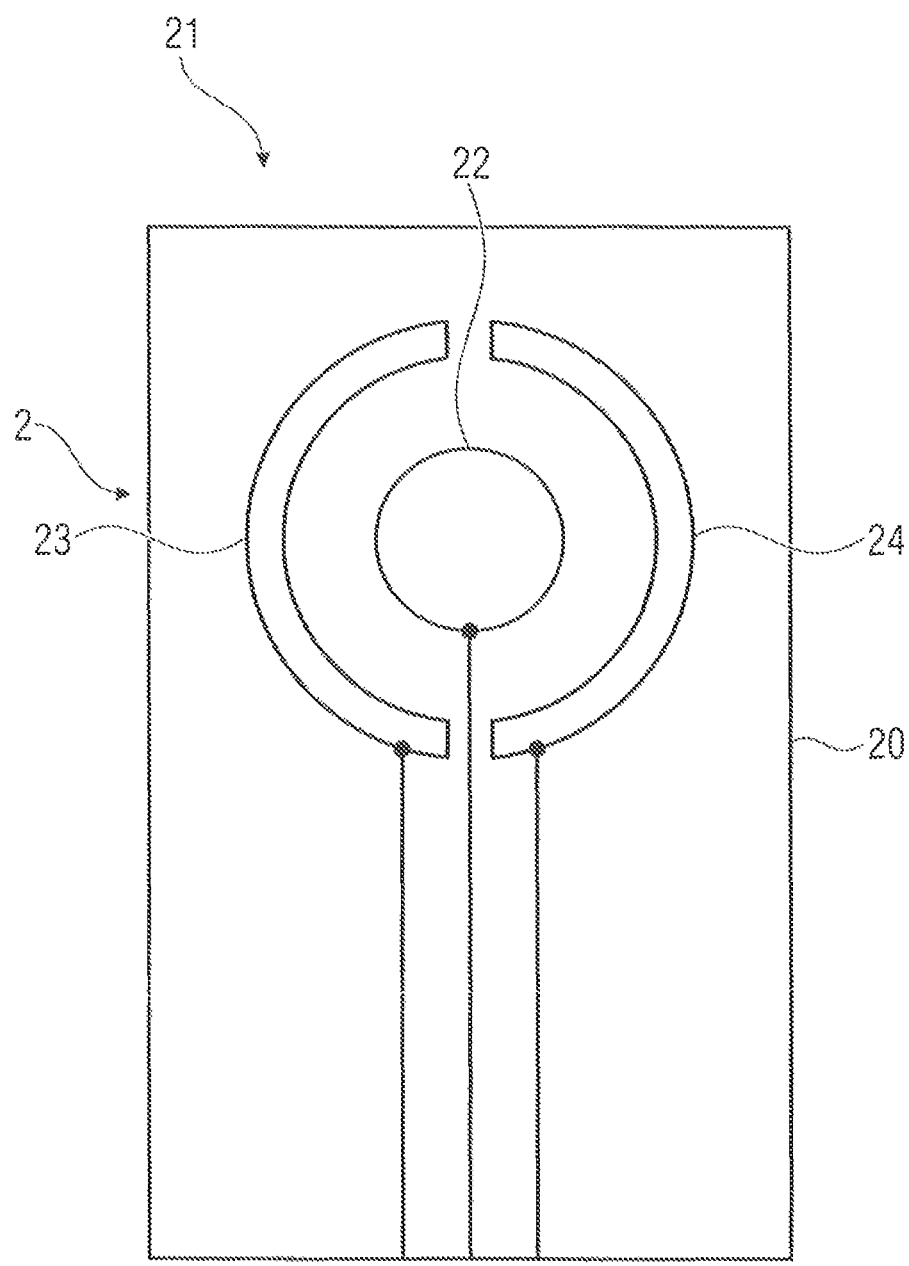

FIG. 3 shows the ion-selective electrode 21 of an analysis sensor 2 deposited on a flexible foil 20. The concentration of an ion is determined via the ion-selective electrode 21. For this, a circular ion selective membrane 22 exists in the illustrated embodiment, which is surrounded by two semi-circular electrodes in the form of a reference electrode 23 and a counter electrode 24. Here, the ion selective membrane 22 separates the in particular humid or at least wet measurement medium (e.g., the flowing body of water or the ground soil or the agricultural product itself) from the electrode assembly. By means of deposited or introduced ionophores, the membrane 22 is adjusted such that only the desired ions can pass the membrane 22. A working electrode whose electric conducting is illustrated by a line is also located at the position of the ion-selective membrane 22.

The concentration of the ions can be determined from the measured electric voltage or the measured electric potential.

Although some aspects have been described in the context of an apparatus, it is obvious that these aspects also represent a description of the corresponding method, such that a block or device of an apparatus also corresponds to a respective method step or a feature of a method step. Analogously, aspects described in the context of a method step also represent a description of a corresponding block or detail or feature of a corresponding apparatus. Some or all of the method steps may be performed by a hardware apparatus (or using a hardware apparatus), such as a microprocessor, a programmable computer or an electronic circuit. In some embodiments, some or several of the most important method steps may be performed by such an apparatus.

Depending on certain implementation requirements, embodiments of the invention can be implemented in hardware or in software or at least partly in hardware or at least partly in software.

Generally, embodiments of the present invention can be implemented as a computer program product with a program code, the program code being operative for performing one of the methods when the computer program product runs on a computer. The program code may, for example, also be stored on a machine readable carrier.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. System for determining and/or monitoring at least one state variable of soil, the system comprising
    at least one analysis sensor, a control apparatus and a read-out apparatus,
        wherein the analysis sensor is configured to be introducible into the soil for remaining within the same,
        wherein the analysis sensor is configured to be sensitive to at least one ion type, and to generate measurement data based on a concentration of the ion type in the soil, wherein the control apparatus is configured to control the analysis sensor with respect to the generation of the measurement data, and wherein the read-out apparatus is configured to read out the measurement data from the analysis sensor, the system further comprising a permanent individual network with a common central network node, wherein several analysis sensors exist, which are sensitive to the same ion type or to different ion types, wherein the several analysis sensors are configured to be wirelessly read-out via the common central network node, wherein the analysis sensors each comprise an RF transmitter for wirelessly transmitting sensor data, wherein the read-out apparatus comprises a first read-out unit and a second read-out unit, the first read-out unit being configured as the common central network node, and wherein the first read-out unit is a stationary read-out unit being arranged remote from the analysis sensors and configured to wirelessly read out the analysis sensors, the first read-out unit being configured to reside inside the soil, and wherein the second read-out unit is a mobile read-out unit configured to be disposed outside the soil and being configured to communicate wirelessly with the first read-out unit when residing inside the soil wherein the analysis sensors and the first read-out unit are configured to be permanently buried in the soil, and wherein the system further comprises at least one energy source that is configured to supply the at least one analysis sensor with energy, wherein the energy source comprises at least one accumulator, and wherein the energy source is configured to be charged inductively.

2. System according to claim 1, wherein the several analysis sensors are configured to be read out individually.

3. System according to claim 1, comprising at least one memory device being configured to store the measurement data and/or data derived from the measurement data.

4. System according to claim 3, wherein the memory device is connected to the read-out apparatus and configured to be introducible into the measurement object for remaining within the same.

5. System according to claim 1, wherein the system comprises at least one evaluation apparatus being configured to evaluate the measurement data with respect to the state variable and/or to derive data from the measurement data.

6. System according to claim 5, wherein the evaluation apparatus is connected to the read-out apparatus and configured to be introducible into the measurement object for remaining within the same.

7. System according to claim 1, wherein the system comprises at least one additional sensor, wherein the additional sensor is an ion-independent sensor differing from the at least one analysis sensor, and wherein the additional sensor is configured to be introducible into the measurement object for remaining within the same and to generate measurement data based on at least one of a temperature, a fill level, a flow rate, a pH value, an electric resistance, an electric conductivity, a proportion of a gas, a proportion of oxygen, or a flow velocity.

8. System according to claim 7, wherein the additional sensor is configured to be read out by the read-out apparatus.

9. System according to claim 8, wherein the system comprises at least one evaluation apparatus being configured to use measurement values of the additional sensors read out by the read-out apparatus together with the measurement data of the at least one analysis sensor for monitoring the state variable of the measurement object.

10. System according to claim 1, wherein the energy source is configured to generate energy by means of energy harvesting.

11. System according to claim 1, wherein the at least one analysis sensor and the read-out apparatus are connected wirelessly and/or by electromagnetic waves with regard to data transmission.

12. System according to claim 1, wherein the at least one analysis sensor comprises at least an ion-selective electrode printed on a foil, an ion-selective membrane comprising at least one ionophore, a reference electrode, and a counter electrode.

13. System according to claim 1, wherein the at least one analysis sensor is configured to measure at least one of nitrate, nitrite, chloride, fluoride, sulfate, ammonium, oxygen, phosphate, potassium, sodium or calcium and/or degradation products of the same, and/or at least one acid, and/or at least one degradation product during a fermentation process.

14. System according to claim 1, wherein the at least one analysis sensor is configured to measure at least one of a biocide, a plasticizer, algae, fungi, spores, bacteria, a toxic agent, a toxin, or a metallic substance.

15. System according to claim 1, wherein the at least one analysis sensor is biodegradable.

* * * * *